United States Patent [19]

Naka et al.

[11] Patent Number: 4,981,855
[45] Date of Patent: Jan. 1, 1991

[54] MEDICAMENT FOR PSORIASIS

[75] Inventors: Takehiko Naka, Hyogo; Taketoshi Saijo, Osaka, both of Japan

[73] Assignee: Takeda Chemical Industries, Ltd., Osaka, Japan

[21] Appl. No.: 388,289

[22] Filed: Aug. 1, 1989

[30] Foreign Application Priority Data

Aug. 2, 1988 [JP] Japan ................................ 63-193655

[51] Int. Cl.$^5$ .......................................... A61K 31/505
[52] U.S. Cl. ..................................... 514/258; 514/863
[58] Field of Search ............................... 514/258, 863

[56] References Cited

U.S. PATENT DOCUMENTS 4,603,203 7/1986 Furakawa et al. .................. 514/262
4,824,848 4/1989 Naka et al. ........................... 514/258

FOREIGN PATENT DOCUMENTS 0166054 12/1984 European Pat. Off. .
0237289  3/1987 European Pat. Off. .

Primary Examiner—Leonard Schenkman
Attorney, Agent, or Firm—Wegner, Cantor, Mueller & Player

[57] ABSTRACT

Disclosed is a method of using medicaments for psoriasis containing 3-aminopyrazolo[3,4-d]pyrimidine compounds or their derivatives such as their salts and their glucuronides, which potently inhibit type III allergic reaction (reversed passive Arthus reaction).

4 Claims, No Drawings

MEDICAMENT FOR PSORIASIS

BACKGROUND OF THE INVENTION

The present invention relates to medicaments for psoriasis containing 3-aminopyrazolo[3,4-d]pyrimidine derivatives.

PRIOR ART

Various pharmaceutical preparations have been proposed for the treatment or prophylaxis of skin diseases. However, no pharmaceutical preparation having a therapeutic or prophylactic effect to psoriasis has yet been discovered On the other hand, 3-aminopyrazolo[3,4-d]pyrimidine derivatives having a diuretic, vasodepressor, analgesic or anti-inflammatory activity have been disclosed, for example, in Japanese Patent Unexamined Publication Nos. 53-31694 (1978), 60-126285 (1985) and 61-5082 (1986). However, a 3-aminopyrazolo[3,4-d]pyrimidine derivative being effective to psoriasis has not been reported.

Psoriasis is one of skin diseases recently increasing in Japan, and is expected to become common in the near future. However, its cause is not yet apparent, though various etiologies are proposed. For example, with respect to abnormalities in the control mechanism of cellular functions, there are observed a number of abnormalities in control in vivo such as (1) the sthenia of glucose utilization in carbohydrate metabolism, (2) serum lipoprotein hypometabolism in fat metabolism, (3) cacochymia through cyclooxygenase and an increase in the production of lipoxygenase metabolites thereby in arachidonic acid metabolism, (4) the activation of the enzyme in polyamine synthesis and a rise in polyamine level in biological amine metabolism, (5) a remarkable reduction in adenylate cyclase activity and an increase in cyclic GMP, (6) the activation of various proteases and the inactivation of their inhibitors, (7) the activation of complement systems, (8) the activation of monocytes and polymorphonuclear leukocytes, and (9) abnormality in cell-mediated immunity. It is therefore very difficult to clarify its main cause. Further, nobody has yet succeeded in an attempt to produce psoriasis on experimental animals. These facts are obstacles to the development in studies on the etiology and treatment of psoriasis.

SUMMARY OF THE INVENTION

Under such circumstances, we attempted to apply the 3-aminopyrazolo[3,4-d]pyrimidine derivatives having potent anti-inflammatory, analgesic, antipyretic and type III allergic reaction(s) depressing activities to the treatment of psoriasis. As a result, it was surprisingly discovered that these derivatives gave a good therapeutic effect to psoriasis. The present invention is based on this discovery.

In accordance with the present invention, there is provided a method for treatment of psoriasis using a medicament containing a 3-aminopyrazolo[3,4-d]pyrimidine derivative having the following formula (I) or a salt thereof as an active ingredient:

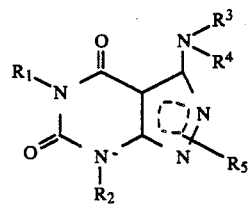

wherein each of $R_1$ and $R_2$ represents an aliphatic hydrocarbon, each of $R_3$, $R_4$ and $R_5$ represents hydrogen, alkyl, acyl or alkoxycarbonyl, the broken line represents that the pyrazole ring has two double bonds, and $R_5$ is bound to either of the 1- or the 2-position of the pyrazole ring.

DETAILED DESCRIPTION OF THE INVENTION

In the above formula (I), examples of aliphatic hydrocarbon groups represented by $R_1$ or $R_2$ include alkyl of about 1 to 6 carbon atoms such as methyl, ethyl, propyl, isopropyl, butyl, isobutyl, pentyl, isopentyl and hexyl, and alkenyl of about 2 to 6 carbon atoms such as vinyl, allyl, 1-propenyl, 2-butenyl, 1,3-butadienyl, and 2-pentenyl. The aliphatic hydrocarbon groups of about 2 to 5 carbon atoms are preferable, and the aliphatic hydrocarbon groups of about 2 to 4 carbon atoms are more preferable.

Preferred examples of the alkyl groups represented by $R_3$ or $R_4$ are alkyl of about 1 to 4 carbon atoms such as methyl, ethyl, propyl, isopropyl, butyl and isobutyl. Examples of the acyl groups represented by $R_3$ or $R_4$ include groups derived from carboxylic acids such as alkanoyl and aromatic carbonyl. Examples of the alkoxycarbonyl represented by $R_3$ or $R_4$ include lower alkoxycarbonyl of 1 to 4 carbon atoms, for example, methoxycarbonyl and ethoxycarbonyl. Preferable are the groups derived from carboxylic acids, namely alkanoyl groups, particularly those containing 7 or less carbon atoms such as acetyl, trifluoroacetyl, propionyl, butyryl, valeryl and cyclohexanecarbonyl, or the aromatic carbonyl groups such as benzoyl.

Preferred examples of the alkyl groups represented by $R_5$ include lower alkyl which may be substituted with halogen or hydroxyl, particularly those of about 1 to 4 carbon atoms such as methyl, ethyl, propyl, butyl and t-butyl. Examples of the acyl groups represented by $R_5$ include radicals derived from carboxylic acids such as alkanoyl and aromatic carbonyl (for example, benzoyl). The preferred alkanoyl groups are those containing 7 or less carbon atoms such as acetyl, trifluoroacetyl, propionyl, butyryl, valeryl and cyclohexanecarbonyl, and the preferred alkoxycarbonyl groups are lower alkoxycarbonyl of 1 to 4 carbon atoms such as methoxycarbonyl and ethoxycarbonyl.

Of the compounds (compound (I)) represented by the above formula (I), the compounds represented by the following formula (I') are preferable:

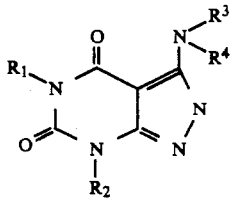

(I')

wherein each of $R_1$ and $R_2$ represents aliphatic hydrocarbon of 2 to 4 carbon atoms, each of $R_3$ and $R_4$ represents hydrogen, alkyl of 1 to 4 carbon atoms, alkanoyl of 7 or less carbon atoms or aromatic carbonyl, and $R_5$ represents hydrogen, alkyl of 1 to 4 carbon atoms or alkoxycarbonyl of 2 to 5 carbon atoms. More preferable are the compounds represented by the formula (I'), wherein each of $R_1$ and $R_2$ is alkyl of 2 to 4 carbon atoms, each of $R_3$ and $R_4$ is hydrogen, methyl or acetyl, and $R_5$ is hydrogen, methyl or methoxycarbonyl.

Examples of the salts of the compounds (I) include the salts of inorganic acids such as hydrochlorides, hidrobromides, sulfates, nitrates and phosphates, and the salts of organic acids such as acetates, tartrates, citrates, fumarates and maleates, which are pharmacologically acceptable.

The compounds (I) are known in the art and can be prepared, for example, by the methods described in Japanese Patent Unexamined Publication Nos. 53-31694 (1978), 60-126285 (1985), 61-5082 (1986) corresponding to U.S. Pat. No. 4,603,203 and European Patent Publication No. 0166054 and 62-22717 (1987) corresponding to U.S. Pat. No. 4,824,848, or by methods similar thereto.

The compounds (I) may be glucuronides (conjugates of glucuronic acid) in which glucuronic acid is bound to the 1- or the 2-position. The glucuronides can be prepared by administering orally or parenterally the compounds (I), for example, to mammals such as a mouse, rat and monkey and then purifying urine or bile collected from the mammals by known methods such as extraction, condensation, neutralization, filtration, column chromatography and thin layer chromatography.

As apparent from Experiments 1 and 2, which will hereinafter be described, the compounds (I) exhibit a depressing activity against the type III allergic reaction (reversed passive Arthus reactions) and are effective for the treatment of psoriasis due to various causes of which the main one is not yet apparent, for example, psoriasis vulgaris, psoriasis pustulosa, psoriasis universalis, psoriasis arthropathica and various symptoms by which psoriasis is accompanied.

Each of the compounds (I) is low in toxicity. In particular, the compound represented by the following formula (A) (referred to as the compound (A)) is low in toxicity as shown in Experiments hereinafter described, and can be used for the treatment of psoriasis with effectiveness and in safety:

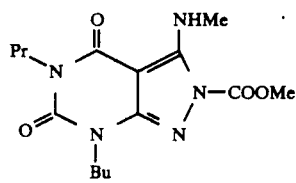

(A)

The medicament for psoriasis of the present invention may be administered as the compounds (I) represented by the formula (I) or their derivatives themselves alone, but are generally administered as various pharmaceutical compositions prepared by mixing the compounds (I) or their derivative with pharmaceutically acceptable additives such as carriers, diluents and vehicles. Examples of the forms of such pharmaceutical compositions include capsules, granules, powders, tablets, pills, syrup, injections, suppositories and ointments.

The therapeutic compositions for psoriasis of the present invention can be administered to mammals including humans orally or parenterally as, for example, ointments, injections or suppositories. When the compounds (I) are glucuronides, the oral administration is preferable.

The dosage is dependent on the object of administration, the route of administration and the symptom. For example, when orally administered to adult patients with psoriasis, it is advantageous that the active ingredients such as the compound (A) are normally administered in one dose of about 0.1 mg/kg to 30 mg/kg of weight, preferably about 0.5 mg/kg to 10 mg/kg of weight, about once to 3 times a day. When administered parenterally, for example, percutaneously (ointments), it is advantageous that the active ingredients such as the compound (A), contained in the about 0.5 to 5%, preferably about 0.8 to 2.5% preparations, are applied to the effected parts in one dose of about 0.1 mg/kg to 30 mg/kg of weight, preferably about 1 mg/kg to 10 mg/kg of weight, about once to 3 times a days.

3-aminopyrazolo[3,4-d]pyrimidine derivatives used in the present invention strongly inhibit type III allergic reactions, which may be responsible for improving effect in psoriasis.

The present invention will be described in more detail in the following Reference Example and Example. It is understood of course that these are not intended to limit the scope of the invention.

In this specification, the following abbreviations are used:
Me: Methyl
Ac: Acetyl
Et: Ethyl
COOMe: Methoxycarbonyl
Pr: Propyl
Bu: Butyl

REFERENCE EXAMPLE

Preparation of 1-deoxy-1-[7-butyl-3-methylamino-5-propylpyrazolo[3,4-d]pyrimidine-4,6(5H,7H)-dione-1-yl]-β-D-glucopyrauronic acid (1a) and 1-deoxy-1-[7-butyl-3-methylamino-5-propylpyrazolo[3,4-d]pyrimidine-4,6(5H,7H)-dione-2-yl]-β-D-glucopyrauronic acid (1b)

To monkeys, 1 g/kg/day of the compound (A) was orally administered for 2 weeks, and thereafter about 4 liter of urine was collected. After the urine was adjusted to pH 6 with 6 N-hydrochloric acid under ice cooling, 600 g of sodium chloride was added thereto, followed by extraction with six 1 liter portions of ethyl acetate. The extracted solution was concentrated to obtain 20 g of syrup. The syrup was dissolved in a small amount of chloroform, and then purified by silica gel chromatography (300 g, eluent: 5–30% methanol/chloroform). From two eluates were obtained a 1-glucuronic acid conjugate (1a) and a 2- glucuronic acid conjugate (1b), respectively. Each was recrystallized from aqueous alcohol to provide white crystals.

1-Glucuronic acid conjugate (1a)

Yield: 1.1 g
Melting point: 202°–205° C. (decomposed)
NMR (d$_6$DMSO) δ: 5.13 (1H, d, 9 Hz, 1'-H)
UVλ$_{max}^{EtOH}$ nm: 280 (sh), 255 (sh), 228

2-Glucuronic acid conjugate (1b)

Yield: 1.0 g
Melting point: 182°–186° C.
NMR (d$_6$-DMSO) δ: 5.61 (1H, d, 9Hz, 1'-H)
UVλ$_{max}^{EtOH}$ nm: 282, 255, 222

EXAMPLE 1

Preparations

The therapeutic compositions for psoriasis containing the compound (A) or the 1-glucuronic acid conjugate of the compound (A) (compound (1a)) can be prepared in accordance with the following formulations:

1. Tablet

| | |
|---|---|
| (1) Compound (A) | 10 mg |
| (2) Lactose | 35 mg |
| (3) Cornstarch | 150 mg |
| (4) Microcrystalline cellulose | 30 mg |
| (5) Magnesium stearate | 5 mg |
| | 230 mg |

(1), (2), (3), two thirds of (4) and one half of (5) are mixed and then granulated. The remainders of (4) and (5) are added to the granules and the mixture is pressed to form a tablet.

2. Capsule

| | |
|---|---|
| (1) Compound (1a) | 10 mg |
| (β) Lactose | 100 mg |
| (3) Microcrystalline cellulose | 70 mg |
| (4) Magnesium stearate | 10 mg |
| | 190 mg |

(1), (2), (3) and one half of (4) are mixed and then granulated. The remainder of (4) is added to the granules and the whole is encapsulated in a gelatin capsule.

3. White petrolatum ointment

| | |
|---|---|
| (1) Compound (A) | 1.25 g |
| (2) White petrolatum | 98.75 g |
| | 100.00 g |

(2) is heated and (1) is dissolved therein, followed by gradual cooling with agitation to form an ointment.

4. Macrogol ointment

| | |
|---|---|
| (1) Compound (A) | 2.5 g |
| (2) Macrogol 400 | 70.0 g |
| (3) Macrogol 4000 | 27.5 g |
| | 100.0 g |

(2) and (3) are heated and (1) is dissolved therein, followed by gradual cooling with agitation to form an ointment.

EXPERIMENT 1

Effect on Type III Allergic Reaction (Reversed Passive Arthus Reaction) in Rats A group consisting of six Jcl:SD rats (7 week old, male) was used. The hair of the back of the animals was cut, under ether anesthesia, and 1 ml each of a 0.5% solution of egg albumin in physiological saline solution was injected into the tail vein of each test animal, followed by intradermal injection of 0.1 ml of rabbit anti-egg albumin antiserum at each of the left and right sides of the back and a further intradermal injection of 0.1 ml of physiological saline solution at the left side. Three hours later, each animal was intraveneously injected with 1 ml of 1% Evans' blue physiological saline solution. Thirty minutes later, the test animals were exfoliated and the area(mm$^2$) of each of the blue spots was measured. The test sample in a dose of 3 mg/kg was orally administered one hour before the injection of egg albumin. By comparing the area(mm$^2$) of the blue spot in the test group (treated group) with that of the control group (untreated group), inhibition rate was determined. The results are shown in Table 1.

TABLE 1

Effect of the Compound (I) on Type III Allergic Reaction (reversed passive Arthus reaction) in Rats

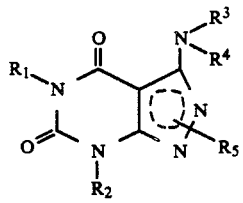

(I)

| No. | R$^1$ | R$^2$ | R$^3$ | R$^4$ | R$^5$ | Inhibition rate (%) Rat, 3 mg/kg P.O. (ID$_{50}$ values, mg/kg, P.O.) |
|---|---|---|---|---|---|---|
| 1$^b$ | Et | Et | H | H | 2-COOMe | 35**$^a$ (13.7) |
| 2 | Pr | Pr | H | H | 2-COOMe | 50** (2.4) |
| 3 | Pr | Pr | Ac | H | H | 55** (2.9) |
| 4 | Pr | Pr | Me | Me | 2-Me | 56** |
| 5 | Pr | Pr | Me | Me | 1-Me | 53** |
| 6 | Pr | Bu | Me | H | 2-COOMe | 43** (5.3) |
| 7 | Bu | Pr | Me | H | 2-COOMe | 49* (3.0) |
| 8 | Bu | Bu | Me | H | 2-COOMe | 30* (30) |
| 9 | Bu | Bu | Me | H | 2-Me | 31* | a*: P < 0.05,
**: P < 0.01 vs. control group
b Compounds 1 to 9 were synthesized by the method described in Japanese Patent Unexamined Publication No. 61-5082 (1986).

EXPERIMENT 2

In place of the oral administration of 3 mg/kg of each specimen, two type of ointments (of which base is white petrolatum) different in specimen content as given in Table 2 and control petrolatum were applied to the reaction sites in an experiment in a similar manner as in Experiment 1. The results are shown in Table 2.

TABLE 2

Effect of Compound (A) Ointments on Rat Reversed Passive Arthus Reaction

| Compound | Dose (mg/site) | Inhibition rate (%) |
|---|---|---|
| Petrolatum (control group) | — | 0 |
| Compound (A) | 1.25 | 46* |

TABLE 2-continued

| | Effect of Compound (A) Ointments on Rat Reversed Passive Arthus Reaction | |
|---|---|---|
| Compound | Dose (mg/site) | Inhibition rate (%) |
| Compound (A) | 2.5 | 59** |

*p < 0.05,
**p < 0.01 vs. control group

It is apparent from Table 2 that the compound (A) significantly depresses the reversed passive Arthus reaction also on percutaneous administration.

EXPERIMENT 3

The acute toxicity of the compound (A) was examined by using Jcl:ICR mice and JcL:Wistar rats. The data of the acute toxicity in intraperitoneal, subcutaneous and oral administrations are shown in Table 3. It is apparent from Table 3 that the compound (A) is low in toxicity and can be safely administered.

TABLE 3

| | Acute Toxicities of the Compound (A) (mg/kg) | | | |
|---|---|---|---|---|
| | Animal | | | |
| | Mouse | Mouse | Rat | Rat |
| Administration | Sex | | | |
| course | Male | Female | Male | Female |
| Intraperitoneal | 1040 | 1260 | 650 | 580 |
| Subcutaneous | >5000 | >5000 | >6500 | >6500 |
| Oral | 4650 | 6310 | 2730 | 2380 |

EXPERIMENT 4

Four-Week Cumulative Skin Irritation Test in Rabbits

[Procedure]

0.25 g of each of white petrolatum (placebo) and 2.5% and 5.0% compound (A) ointments (of which base is white petrolatum) was applied to 2.5×2.5 cm test sites (normal skin and damaged skin) formed on the skin of the backs of rabbits once a day for 4 weeks. The skin was observed daily according to the method of Draize [J. H. Draize et al., *J. Pharmacol. Exp. Therap.* 82, 337 (1944)]. On the day succeeding the completion of the administration, postmortem examinations were carried out and histopathologic examinations were conducted for the skin of the administrated sites.

[Results]

The 2.5% and 5% compound (A) ointments showed no cumulative skin irritation in this Experiment 4.

What is claimed is:

1. A method for the treatment of a human patient with psoriasis, which comprises administering to such patient an effective amount of a compound having the following formula or a pharmacologically acceptable salt thereof or a glucuronide thereof:

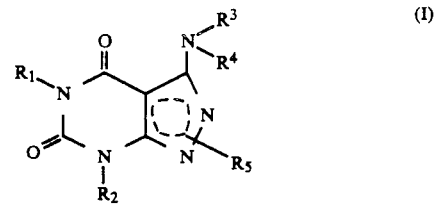

wherein each of $R_1$ and $R_2$ represents an aliphatic hydrocarbon, each of $R_3$, $R_4$ and $R_5$ represents hydrogen, alkyl, acyl or alkoxycarbonyl, the broken line represents that the pyrazole ring has two double bonds, and $R_5$ is bound to either of the 1- or the 2-position of the pyrazole ring.

2. The method according to claim 1, wherein the compound has the following formula:

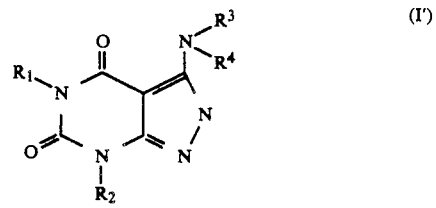

wherein each of $R_1$ and $R_2$ represents an aliphatic hydrocarbon of 2 to 4 carbon atoms, each of $R_3$ and $R_4$ represents hydrogen, alkyl of 1 to 4 carbon atoms, alkanoyl of 7 or less carbon atoms or aromatic carbonyl, and $R_5$ represents hydrogen, alkyl of 1 to 4 carbon atoms or alkoxycarbonyl of 2 to 5 carbon atoms.

3. The method according to claim 2, wherein each of $R_1$ and $R_2$ is alkyl of 2 to 4 carbon atoms, each of $R_3$ and $R_4$ is hydrogen, methyl or acetyl, and $R_5$ is hydrogen, methyl or methoxycarbonyl.

4. The method according to claim 3, wherein $R_1$ is propyl, $R_2$ is butyl, $R_3$ and $R_4$ are hydrogen and methyl, respectively, and $R_5$ is methoxycarbonyl.

* * * * *